(12) United States Patent
Ivell

(10) Patent No.: US 6,534,634 B1
(45) Date of Patent: Mar. 18, 2003

(54) DIAGNOSTIC AGENT AND METHOD TO DETERMINE PREGNANCY IN RUMINANTS

(75) Inventor: Richard Ivell, Hamberg (DE)

(73) Assignee: IHF Institut fur Hormon- und Fortpflanzungsforschung GmbH, Hamberg (DE)

( * ) Notice: Subject to any disclaimer, the term of this patent is extended or adjusted under 35 U.S.C. 154(b) by 0 days.

(21) Appl. No.: 09/269,410

(22) PCT Filed: Sep. 17, 1997

(86) PCT No.: PCT/EP97/05075

§ 371 (c)(1),
(2), (4) Date: May 20, 1999

(87) PCT Pub. No.: WO98/13693

PCT Pub. Date: Apr. 2, 1998

(30) Foreign Application Priority Data

Sep. 27, 1996 (DE) .......................................... 196 41 378

(51) Int. Cl.⁷ ............................................. C07K 16/00
(52) U.S. Cl. ................... 530/387.9; 530/389.2; 530/397; 530/399; 530/303; 435/7.9; 424/198.1
(58) Field of Search ........................ 435/7.9, 65, 545, 435/814, 817; 514/12, 8; 530/389.2, 397, 399, 303, 387.9; 424/198.1

(56) References Cited

U.S. PATENT DOCUMENTS

| | | | | |
|---|---|---|---|---|
| 4,686,103 A | * | 8/1987 | Anderson | 424/97 |
| 5,166,190 A | * | 11/1992 | Mather et al. | 514/8 |
| 5,279,942 A | * | 1/1994 | Kuniyuki | 435/7.9 |
| 5,304,603 A | * | 4/1994 | Cheng et al. | 514/12 |
| 5,811,395 A | * | 9/1998 | Schwabe et al. | 514/12 |
| 5,911,997 A | * | 6/1999 | Schwabe et al. | 424/198.1 |
| 5,959,075 A | * | 9/1999 | Lok et al. | 530/303 |
| 6,046,028 A | * | 4/2000 | Conklin et al. | 435/69.1 |

OTHER PUBLICATIONS

Adham, IM et al, Journal od Biological Chemistry, Dec. 15, 1993, vol. 268 (35), pp. 26668–26672.*
Adham et al, Journal of Breeding and Genetics, vol. 113(4–5), pp. 229–235, 1996.*
Bravo, P. Walter et al, JAVMA, vol. 208 (12), Jun. 15, 1996, pp. 2027–2030.*
Bryant–Greenwood et al, Journal of Endocrinology, vol. 81(3), pp. 239–247, Jun. 1979.*
Brenner, SH et al, Obstetrics and Gynecology, vol. 66(1), pp. 46–49, Jul. 1985, (abstract only).*
Bullesbach, EE et al, Journal of Biological Chemistry, vol. 270(27), pp. 16011–16015, Jul. 7, 1995.*
Bullesbach, E et al, Life Sciences, Aug. 24, 1987, vol. 41(8), pp. 989–994.*
Burkhardt, E et al, Genomics, Mar. 1, 1994, vol. 20)1), pp. 13–19.*
Chamley, WA et al, Journal of Reproduction and Fertility, vol. 45(3), pp. 455–461, 1975(abstract only).*
Dubois, W et al, Society for the Study of Reproduction Nineteenth Annual Meeting, Jul. 14–17, 1986, Ithaca, NY (USA), (abstract #159).*

(List continued on next page.)

Primary Examiner—Mark Navarro
Assistant Examiner—Ginny Allen Portner
(74) Attorney, Agent, or Firm—Nixon & Vanderhye P.C.

(57) ABSTRACT

The present invention relates to diagnosis aids and processes for detecting pregnancy in ruminants based on the relaxin-like factor detectable in ruminants. Antibodies against the relaxin-like factor from ruminants as well as against fragments and/or active derivatives of the same with the same immunogenicity are also provided.

13 Claims, 8 Drawing Sheets

```
GGCAACGAGGGGCCCGGTGCCTCTCACTACCATGGACCGTCGTC   45
                              M  D  R  R         4
CGCTCACCTGGGCTCTGGTGCTGCTGGGCCCGGCCCTTGCAATCG   90
 P  L  T  W  A  L  V  L  L  G  P  A  L  A  I   19
                 signal peptide
CCCTCGGTCCTGCAGCCGCGCAGGAGGCGGCCTGAAGAAACTGTGTG  135
 A  L  G  P  A  A  A  Q  E  A  P  E  K  L  C   34
                                B-domain
GCCACCACTTCGTGCGGCGGCTCGTGCGGCTGTGCGGCGGACCGC  180
 G  H  H  F  V  R  A  L  V  R  L  C  G  G  P   49
GCTGGTCTTCCGAGGAGGACGGGCGACCTGTGGCTGGCGGCGACC  225
 R  W  S  S  E  E  D  G  R  P  V  A  G  G  D   64
GTGAGCTCCTACGGTGGCTGGAAGGACAACATCTCCTCCATGGGC  270
 R  E  L  L  R  W  L  E  G  Q  H  L  L  H  G   79
                    C-domain
TGATGGCCAGTGGGGACCCCGTGCTGGTACTGGCCCCACAGCCCC  315
 L  M  A  S  G  D  P  V  L  V  L  A  P  Q  P   94
TGCCCCAGGCTTCTCGCCATCACCACCACCGCCGAGCAACTGCCA  360
 L  P  Q  A  S  R  H  H  H  R  R  A  T  A    109
TCAACCCTGCCCGCCACTGCTGCCTCAGCGGCTGCACCCGGCAAG  405
 I  N  P  A  R  H  C  C  L  S  G  C  T  R  Q   124
                     A-domain
ACCTGCTGACCCTCTGTCCCCACTGAATCCTCCTGGGGCGTGGCT  450
 D  L  L  T  L  C  P  H  *                     132
TGGGGGAGCCTGAGACCCACAGGAGTCCAGTTTGGTGAACTCCTG  495
ATGCCACACAGCACCATGAAACCCCACATCTAGGGGGATGTTGTT  540
GATTACCTCCTAGGACAAGGTGCTCACCACCTCACCCAGGCCACC  585
TGTCCTCTGGGGGATCAACTAGGGATACCACCAGACCCCAAATCT  630
GGCTTGGAGGATCCTTGGTTTTGCAGAGATGCCAGACACTCTTCT  675
CAAATGTTCTCACCTCAGAGGAGCCCCAGGTGCCCCACTCCCTGC  720
CTTTGACACCCTTCTTGTTGTCTCCAATAGTAAATAAATAAGA   765
TGCCTGC poly(A)                      AAAT    772
```

OTHER PUBLICATIONS

Eldridge, R et al, Endocrinology 7th International Congress, Quebec City (Canada) Jul. 1–7, 1984 (abstract only).*

Georges, D et al, Gen. Comp. Endocrinol., vol. 79(3), pp. 423–428, 1990.*

Ivell, R, Reviews of Reproduction, Sep. 1997, vol. 2(3), pp. 133–138.*

Larkin, LH et al, Acta Endocrinology, Nov. 1979, vol. 92(3), pp. 568–576.*

O'Byrne et al, Proceedings of the Society for Experimental Biology and Medicine, vol. 152(2), pp. 272–276, Jun. 1976.*

Patterson, J et al, 27th Annual Meeting of the Endocrine Society of Australia, Melbourne, Victoria, Australia, Aug. 26–29, 1994, Endocr. Soc. Aust. Proc. 27(0), 1984 (received 1985), p. 71.*

Pusch, W et al, Endrocrinology, vol. 137(7), pp. 3009–3013, Jul. 1996.*

Roche, P.J et al, Molecular and Cellular Endocrinology, vol. 121, Jul. 1996, pp. 171–177.*

Sokol, RZ et al, Annual Meeting of the American Federation of Clinical Research (Western Section), Carmel, California, USA, Feb. 3–6, 1987, Clin. Res, vol. 35(1), 1987, abstract:123A.*

Stewart, DR et al, Biol. Reprod. vol. 38(suppl. 1), abstract 262, p. 136, Aug. 1–4, 1988.*

Tashima, LS et al, 42 nd Annual Meeting of the Society for Gynecological Investigation, Chicago, ILL, Mar. 15–18, 1995.*

Rettenberget, G et al, Mammalian genome, vol. 5(5), pp. 307–309, May 1994.*

Wathes, DC et al, Journal of Reproduction and Fertility, vol. 84(1), Sep. 1988, pp. 247–257.*

Zimmermann, S et al, Molecular Reproduction and development, May 1997, vol. 47(1), pp. 30–38.*

Eddie, LW et al, The Lancet, p. 1344–1346, Jun. 14, 1986.*

Hartung et al, Chapter 30, in Progress in Relaxin Research, The proceedings of the second International Congress on the Hormone Relaxin held in Adelaide, South Australia, pp. 439–456, 1995.*

Anderson et al, Chapter 29, in Progress in Relaxin Research, The proceedings of the second International Congress on the Hormone Relaxin held in Adelaide, South Australia, pp. 428–438, 1995.*

M.J. Fields et al.: "Chemistry of bovine relaxin" Advances in Experimental Medicine and Biology, Bd. 143, 1982, New York NY USA, Seiten 191–207, XP002053014 siehe Seite 201, Zeile 1—Zeile 24; Abbildung 4.

M.J. Fields et al.; "Evidence for relaxin in corpora lutea of late pregnant cows." Endocronology, vol. 107, No. 4, 1980, Washington DC USA, pp. 869–876, XP002053016 see whole document.

* cited by examiner

Fig. 1

```
GGCAACGAGGGGGCCCGGTGCCTCTCACTACCATGGACCGTCGTC    45
                                  M  D  R  R     4
                                  ←
CGCTCACCTGGGCTCTGGTGCTGCTGGGCCCGGCCCTTGCAATCG    90
 P  L  T  W  A  L  V  L  L  G  P  A  L  A  I    19
─────────────── signal peptide ───────────────
CCCTCGGTCCTGCAGCCGCGCAGGAGGCGCCTGAGAAACTGTGTG   135
 A  L  G  P  A  A  A  Q  E  A  P  E  K  L  C    34
──────────────→  ←─────────── B-domain ──────
GCCACCACTTCGTGCGCGCGCTCGTGCGGCTGTGCGGCGGACCGC   180
 G  H  H  F  V │R  A  L  V  R│ L  C  G  G  P    49
               └──────────────┘
GCTGGTCTTCCGAGGAGGACGGGCGACCTGTGGCTGGCGGCGACC   225
 R  W  S  S  E  E  D  G  R  P  V  A  G  D       64
─────────────→   ←──────────
GTGAGCTCCTACGGTGGCTGGAAGGACAACATCTCCTCCATGGGC   270
 R  E  L  L  R  W  L  E  G  Q  H  L  L  H  G    79
──────────────── C-domain ───────────────
TGATGGCCAGTGGGGACCCCGTGCTGGTACTGGCCCCACAGCCCC   315
 L  M  A  S  G  D  P  V  L  V  L  A  P  Q  P    94

TGCCCCAGGCTTCTCGCCATCACCACCACCGCCGAGCAACTGCCA   360
 L  P  Q  A  S  R  H  H  H  H  R  R  A  T  A   109
                                   ──────→ ←──
TCAACCCTGCCCGCCACTGCTGCCTCAGCGGCTGCACCCGGCAAG   405
 I  N  P  A  R  H  C  C  L  S  G  C  T  R  Q   124
──────────────── A-domain ─────────────
ACCTGCTGACCCTCTGTCCCCACTGAATCCTCCTGGGGCGTGGCT   450
 D  L  L  T  L  C  P  H  *                     132
──────────────→
TGGGGGAGCCTGAGACCCACAGGAGTCCAGTTTGGTGAACTCCTG   495

ATGCCACACAGCACCATGAAACCCCACATCTAGGGGGATGTTGTT   540

GATTACCTCCTAGGACAAGGTGCTCACCACCTCACCCAGGCCACC   585

TGTCCTCTGGGGGATCAACTAGGGATACCACCAGACCCCAAATCT   630

GGCTTGGAGGATCCTTGGTTTTGCAGAGATGCCAGACACTCTTCT   675

CAAATGTTCTCACCTCAGAGGAGCCCCAGGTGCCCCACTCCCTGC   720

CTTTGACACCCTTCTTGTTGTCTCCTCAATAGTAAATAAATAAGA   765
                                    ─────  ────
TGCCTGC  poly(A)           AAAT                772
```

Fig. 2

```
                       ←—signal peptide——→ ←————————————————————
cattle    MDRRPLTWALVLLGPALAIALGPAAAQEAPEKLCGHHF-VRALVR
          **  **************  ** ************* ******
pig       MDPHPLTWALVLLGPALALSRAPAPAQEAPEKLCGHHF-VRALVR
human     MDPRLPAWALVLLGPALVFALGPAPTPEMRGKLCGHHF-VRALVR
mouse     M-RAPLLLMLLALGSALRSS--PQP-PEARAKLCGHHKLVRTLVR —B-domain—→ ←——————————— C-domain ———
          LCGGPRWSSEEDGRPVAGGDRELLRWLEGQHLLHGLMASGDPVLV
          ********  *  *** ********  ******* ********  **
          LCGGPRWSPE-DGRAVAGGDRELLQWLEGQHLFHGLMASGDPMLV
          VCGGPRWSTE-ARRPAAGGDRELLQWLERRHLLHGLVADSNLTLG
          VCGGPRWSPE-ATQPVETRDRELLQWLEQRHLLHALVVADVDPA- ——————————→ ←—— A-domain ——————————→
          LAPQPLPQASRHHHHHRRATAINPARHCCLSGCTRQDLLTLCPH
          *****  ****  ******  * *************************
          LAPQPPPQASGHHHHHRRAAATNPARHCCLSGCTRQDLLTLCPH
          PGLQPLPQTSHHHRHHRAAATNPARYCCLSGCTQQDLLTLCPY
          LDPQLPRQASQ--RQRRSAATNAVHRCCLTGCTQQDLLGLCPH
```

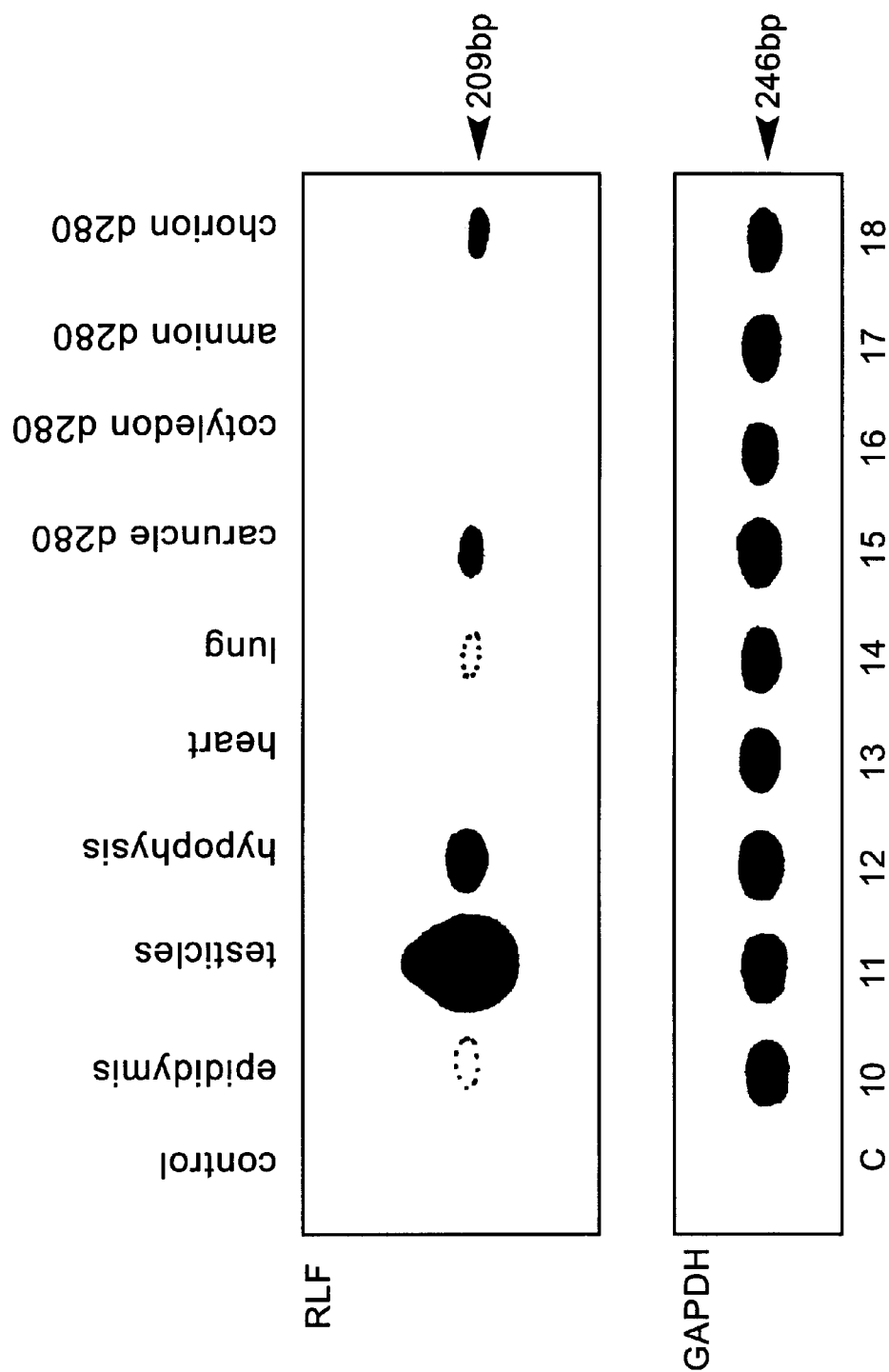

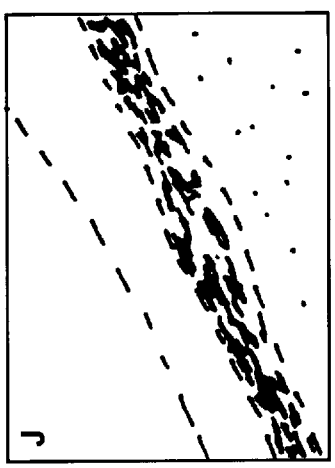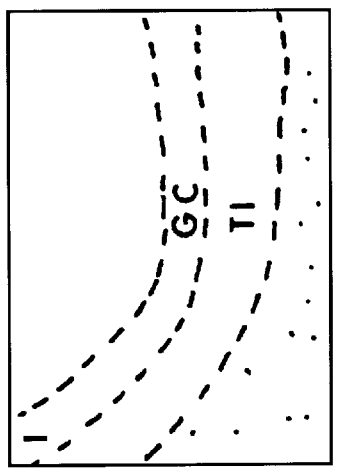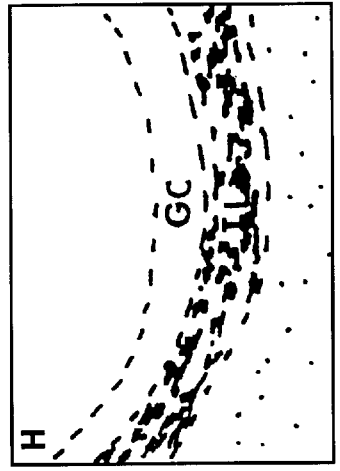
Fig. 6C
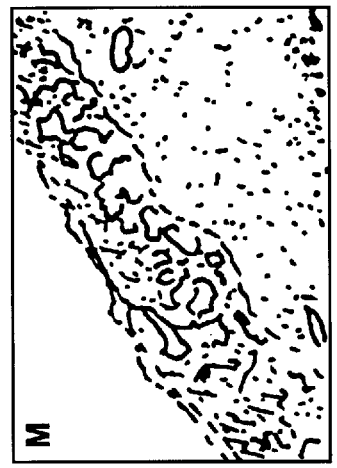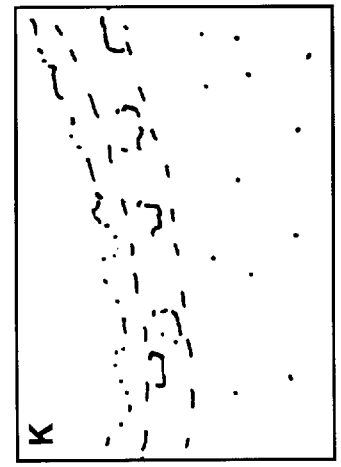
Fig. 6D

SEQUENCE LISTING

<160> NUMBER OF SEQ ID NOS: 12

<210> SEQ ID NO 1
<211> LENGTH: 772
<212> TYPE: DNA
<213> ORGANISM: cattle
<220> FEATURE:
<221> NAME/KEY: CDS
<222> LOCATION: (33)..(428)

<400> SEQUENCE: 1

```
ggcaacgagg gggcccggtg cctctcacta cc atg gac cgt cgt ccg ctc acc      53
                                    Met Asp Arg Arg Pro Leu Thr
```

```
                          1               5
tgg gct ctg gtg ctg ctg ggc ccg gcc ctt gca atc gcc ctc ggt cct    101
Trp Ala Leu Val Leu Leu Gly Pro Ala Leu Ala Ile Ala Leu Gly Pro
        10              15              20 gca gcc gcg cag gag gcg cct gag aaa ctg tgt ggc cac cac ttc gtg    149
Ala Ala Ala Gln Glu Ala Pro Glu Lys Leu Cys Gly His His Phe Val
    25              30              35 cgc gcg ctc gtg cgg ctg tgc ggc gga ccg cgc tgg tct tcc gag gag    197
Arg Ala Leu Val Arg Leu Cys Gly Gly Pro Arg Trp Ser Ser Glu Glu
40              45              50              55 gac ggg cga cct gtg gct ggc ggc gac cgt gag ctc cta cgg tgg ctg    245
Asp Gly Arg Pro Val Ala Gly Gly Asp Arg Glu Leu Leu Arg Trp Leu
            60              65              70 gaa gga caa cat ctc ctc cat ggg ctg atg gcc agt ggg gac ccc gtg    293
Glu Gly Gln His Leu Leu His Gly Leu Met Ala Ser Gly Asp Pro Val
            75              80              85 ctg gta ctg gcc cca cag ccc ctg ccc cag gct tct cgc cat cac cac    341
Leu Val Leu Ala Pro Gln Pro Leu Pro Gln Ala Ser Arg His His His
        90              95              100 cac cgc cga gca act gcc atc aac cct gcc cgc cac tgc tgc ctc agc    389
His Arg Arg Ala Thr Ala Ile Asn Pro Ala Arg His Cys Cys Leu Ser
    105             110             115 ggc tgc acc cgg caa gac ctg ctg acc ctc tgt ccc cac tgaatcctcc    438
Gly Cys Thr Arg Gln Asp Leu Leu Thr Leu Cys Pro His
120             125             130 tggggcgtgg cttgggggag cctgagaccc acaggagtcc agtttggtga actcctgatg    498
ccacacagca ccatgaaacc ccacatctag ggggatgttg ttgattacct cctaggacaa    558
ggtgctcacc acctcaccca ggccacctgt cctctggggg atcaactagg gataccacca    618
gaccccaaat ctggcttgga ggatccttgg ttttgcagag atgccagaca ctcttctcaa    678
atgttctcac ctcagaggag ccccaggtgc cccactccct gcctttgaca cccttcttgt    738
tgtctcctca atagtaaata aataagatgc ctgc                                  772

<210> SEQ ID NO 2
<211> LENGTH: 132
<212> TYPE: PRT
<213> ORGANISM: cattle

<400> SEQUENCE: 2

Met Asp Arg Arg Pro Leu Thr Trp Ala Leu Val Leu Leu Gly Pro Ala
 1               5                  10                  15

Leu Ala Ile Ala Leu Gly Pro Ala Ala Ala Gln Glu Ala Pro Glu Lys
            20                  25                  30

Leu Cys Gly His His Phe Val Arg Ala Leu Val Arg Leu Cys Gly Gly
        35                  40                  45

Pro Arg Trp Ser Ser Glu Glu Asp Gly Arg Pro Val Ala Gly Gly Asp
    50                  55                  60

Arg Glu Leu Leu Arg Trp Leu Glu Gly Gln His Leu Leu His Gly Leu
65                  70                  75                  80

Met Ala Ser Gly Asp Pro Val Leu Val Leu Ala Pro Gln Pro Leu Pro
                85                  90                  95

Gln Ala Ser Arg His His His Arg Arg Ala Thr Ala Ile Asn Pro
            100                 105                 110

Ala Arg His Cys Cys Leu Ser Gly Cys Thr Arg Gln Asp Leu Leu Thr
        115                 120                 125

Leu Cys Pro His
```

-continued

130

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
cgctggtgcg ggtgtgcgg                                                19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
gtcttgctgg gtgcagcc                                                 18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
ccgccagcca caggtcgc                                                 18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
cgagcgcgcg cacgaagtgg                                               20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
cgcgctggtc ttccgagg                                                 18

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
ggccccacag cccctgcccc agg                                           23

<210> SEQ ID NO 9
<211> LENGTH: 131
<212> TYPE: PRT
<213> ORGANISM: PIG

<400> SEQUENCE: 9

Met Asp Pro His Pro Leu Thr Trp Ala Leu Val Leu Leu Gly Pro Ala
 1               5                  10                  15

Leu Ala Leu Ser Arg Ala Pro Ala Gln Glu Ala Pro Glu Lys
             20                  25                  30

Leu Cys Gly His His Phe Val Arg Ala Leu Val Arg Leu Cys Gly Gly
             35                  40                  45

Pro Arg Trp Ser Pro Glu Asp Gly Arg Ala Val Ala Gly Gly Asp Arg
     50                  55                  60

Glu Leu Leu Gln Trp Leu Glu Gly Gln His Leu Phe His Gly Leu Met
 65                  70                  75                  80

Ala Ser Gly Asp Pro Met Leu Val Leu Ala Pro Gln Pro Pro Gln
                 85                  90                  95

Ala Ser Gly His His His Arg Arg Ala Ala Ala Thr Asn Pro Ala
                100                 105                 110

Arg His Cys Cys Leu Ser Gly Cys Thr Arg Gln Asp Leu Leu Thr Leu
            115                 120                 125

Cys Pro His
        130

<210> SEQ ID NO 10
<211> LENGTH: 131
<212> TYPE: PRT
<213> ORGANISM: HUMAN

<400> SEQUENCE: 10

Met Asp Pro Arg Leu Pro Ala Trp Ala Leu Val Leu Leu Gly Pro Ala
 1               5                  10                  15

Leu Val Phe Ala Leu Gly Pro Ala Pro Thr Pro Glu Met Arg Gly Lys
             20                  25                  30

Leu Cys Gly His His Phe Val Arg Ala Leu Val Arg Val Cys Gly Gly
             35                  40                  45

Pro Arg Trp Ser Thr Glu Ala Arg Arg Pro Ala Ala Gly Gly Asp Arg
     50                  55                  60

Glu Leu Leu Gln Trp Leu Glu Arg Arg His Leu Leu His Gly Leu Val
 65                  70                  75                  80

Ala Asp Ser Asn Leu Thr Leu Gly Pro Gly Leu Gln Pro Leu Pro Gln
                 85                  90                  95

Thr Ser His His His Arg His Arg Ala Ala Ala Thr Asn Pro Ala
                100                 105                 110

Arg Tyr Cys Cys Leu Ser Gly Cys Thr Gln Gln Asp Leu Leu Thr Leu
            115                 120                 125

Cys Pro Tyr
        130

<210> SEQ ID NO 11
<211> LENGTH: 125
<212> TYPE: PRT
<213> ORGANISM: MOUSE

<400> SEQUENCE: 11

-continued

```
Met Arg Ala Pro Leu Leu Leu Met Leu Leu Ala Leu Gly Ser Ala Leu
 1               5                  10                  15

Arg Ser Ser Pro Gln Pro Pro Glu Ala Arg Ala Lys Leu Cys Gly His
                20                  25                  30

His Lys Leu Val Arg Thr Leu Val Arg Val Cys Gly Gly Pro Arg Trp
            35                  40                  45

Ser Pro Glu Ala Thr Gln Pro Val Glu Thr Arg Asp Arg Glu Leu Leu
     50                  55                  60

Gln Trp Leu Glu Gln Arg His Leu Leu His Ala Leu Val Val Ala Asp
 65                  70                  75                  80

Val Asp Pro Ala Leu Asp Pro Gln Leu Pro Arg Gln Ala Ser Gln Arg
                85                  90                  95

Gln Arg Arg Ser Ala Ala Thr Asn Ala Val His Arg Cys Cys Leu Thr
                100                 105                 110

Gly Cys Thr Gln Gln Asp Leu Leu Gly Leu Cys Pro His
            115                 120                 125

<210> SEQ ID NO 12
<211> LENGTH: 5
<212> TYPE: PRT
<213> ORGANISM: BOVINE

<400> SEQUENCE: 12

Arg Ala Leu Val Arg
 1               5
```

DIAGNOSTIC AGENT AND METHOD TO DETERMINE PREGNANCY IN RUMINANTS

This application is a national phase of PCT/EP97/05075, filed Sep. 17, 1997, which is based on DE 196 41 378.8, filed Sep. 27, 1996.

The present invention relates to diagnosis aids and processes for detecting pregnancy in ruminants based on the relaxin-like factor detectable in ruminants. Antibodies against the relaxin-like factor of ruminants as well as against fragments and/or active derivatives of the same with the same immunogenicity are also provided.

At present, several immunological processes exist for determining the pregnancy of numerous mammals. Thus it is already known for example that pregnancies in women can be reliably detected by the detection of specific antibodies against the human chorionic gonadotrophin in the urine of the person to be examined, hemagglutination inhibition test, latex agglutionation inhibition tests or radioimmunological detection of β-HCG being used in particular. In addition it is possible to detect pregnancy in several mammals by determining the yellow body hormone relaxin formed above all in the uterus and placenta during the pregnancy, which very early on during the pregnancy reaches a certain level which by contrast is never exceeded in the normal non-pregnant cycle. It was even shown that a specific increase in the relaxin in the peripheral serum takes place during a very early stage, namely even before the nidation of the blastocytes and even before a clear positive HCG test (D. R. Stewart et al., Relaxin in the peri-implantation period, J.Clin. Endocrinol. Metab., 70: 1771–1773 (1990)). Consequently, it has been proposed to provide alternative pregnancy tests on the basis of detecting relaxin. For example, processes are described in U.S. Pat. No. 5,108,897 for determining the pregnancy of bitches, with which the relaxin values detectable in certain body fluids or tissues of the animals in the case of pregnancy are measured.

Alongside relaxin, another peptide hormone, called relaxin-like factor (abbreviation: RLF) has recently been identified (E. Bullesbach et al., A novel Leydig cell cDNA-derived protein is a relaxin-like factor, J. Biol. Chem., 270: 16011–16015 (1995)). While the function of regulating the physiology of female animals of most mammal types is essentially attributed to relaxin, RLF seems to be expressed exclusively in the Leydig cells of the male gonads in most types according to current knowledge, as substantial amounts of specific mRNA were detected in this tissue (W. Pusch et al., Molecular cloning and expression of the relaxin-like factor from the mouse testis, Endocrinology, 137 (1996, printing); I. M. Adham et al., Cloning of a cDNA for a novel insulin-like peptide of the testicular Leydig cells, J. Biol. Chem., 268: 26668–26672 (1993)). By using the reverse transcription polymerase chain reaction (RT-PCR) and succeeding Northern hybridisation, specific signals for RLF-mRNA were however also detected in ovaries and trophoblasts of humans (L. Tashima et al., The human Leydig insulin-like (Ley-I-L) gene is expressed in the corpus luteum and trophoblast, J. Clin. Endocrinol. Metab., 80: 707–710 (1995)).

However, ruminants occupy a special place amongst mammals insofar as, although they show clear signs of a relaxin-dependent physiology in the case of pregnancy, no expression of a relaxin gene has so far been detected (S. Hartung et al., The search for ruminant relaxin, in: A. H. McLennan, G. Tregear and G. D. Bryant-Greenwood (Publ.) "Progress in Relaxin Research", Singapore, World Scientific Publishing, pp. 439–456 (1995)). A deletion in the relaxin gene has in fact been established in sheep (P. J. Roche et al., A single copy relaxin-like gene sequence is present in sheep, Mol. Cell. Endocrinol., 91: 21–28 (1993)).

As the yellow body hormone relaxin has thus up until now been detected only in non-ruminant species such as humans, horses, cats, pigs, rats, mice, guinea pigs and hamsters, and the pregnancy-dependent gonadotrophin is detectable exclusively in primates and horses, there is a considerable need for diagnostic possibilities for determining pregnancy in other mammal types, such as in particular in ruminants.

The object of the present invention is consequently to provide diagnosis aids and processes as well as suitable substances for same with which a pregnancy can be reliably detected in ruminants and particularly in cattle.

To achieve the object, the diagnosis aid for detecting pregnancy in ruminants, characterized in that it comprises antibodies against the relaxin-like factor of ruminants or fragments of the same with the same immunospecificity, the process for detecting the pregnancy of ruminants, characterized in that body fluids or tissue are removed from the animal to be examined, in which the relaxin-like factor is detectable during the pregnancy of the animal and the presence of the relaxin-like factor is detected in the body fluid or the tissue of the animal. The object of the invention is also to provide antibodies directed against the relaxin-like factor of ruminants as such or against fragments and/or active derivatives of the same with the same immunogenicity; the use of the same for detecting pregnancy in ruminants; and further versions of the diagnosis aid, processes of the using the same and antibodies useful therein are also further described herein.

Within the framework of the research efforts which finally led to the present invention, a relaxin-like factor has now also been detected in female ruminants and particularly in cows, which is expressed in very large quantities in the yellow body (corpus luteum). The expression patterns of the RLF gene of cattle are very similar to those of the human relaxin genes with an increase in the late luteal phase and with continuing expression into the pregnancy, whereby the applicability of the means and processes proposed according to the invention for determining the pregnancy of ruminants and in particular cattle is emphasized.

The RLF protein of pigs is known to have a primary structure which is similar to an A-, B-, C- (connecting) peptide of the primary structure of insulin. All three peptide regions are contained in the RLF precursor protein which is cleaved post-translationally into its components. The A- and B- peptides form a factor present as a heterodimer, while the C-peptide is presumably discarded. The primary sequence of the cattle RLF shown in FIG. 1 is similar to that of pigs in its primary structure and presumably leads equally to a heterodimeric factor. The RLF-protein contains additionally a signal sequence at the N terminus which is used for the cotranslational introduction of the molecule into the secretory system of the cells and is subsequently cleaved off. As this structure also exists in the RLF-precursor in cattle, it is to be assumed that this protein is also secreted into the blood path and can accordingly be detected.

Within the framework of the invention, the entire coding region of the RLF-gene of the cattle has been cloned and sequenced with the help of the RT-PCR (see Example 1). Furthermore, with the help of the Northern RNA hybridisation as well as the RT-PCR, a large quantity of tissue of the female and male cattle was examined with regard to the expression of the gene (see Example 2). The results show that the RLF of the cattle is expressed exclusively in the Leydig cells of the bull and in the yellow bodies of the cow. The amino acid sequence shown in FIG. 1 (SEQ ID NO: 2) of the relaxin-like factor of ruminants according to the invention offers the possibility of providing, with the help of established processes, polyclonal and monoclonal antibodies or fragments of the same with the same immunospecificity for use in diagnosis aids and immunological detecting processes. Such antibodies can be prepared on the basis of the complete RLF as well as on the basis of fragments and/or active derivatives of the same with the same immunogenicity.

The term "antibody" used within the framework of the present description relates to a protein which consists of one or more polypeptides which are essentially coded by antibody genes. These genes include different genes for constant regions as well as those for the multitude of variable regions of antibodies. The antibodies according to the invention with a specificity for the RLF of ruminants can be used when solubized or immobilized in a multitude of forms, including in particular Fv-, Fab-. Fab'-, F(ab')$_2$-fragments as well as single chains.

Preferred antibodies are polyclonal and in particular monoclonal antibodies and fragments of the same, which have the same characteristics regarding the interaction with the RLF of ruminants. The antibodies are particularly preferably provided with a detectable marker—either directly or via a second immunoglobulin-specific antibody. Photoactivatable compounds such as biotin, radioactive isotopes such as indium, iodine, yttrium, technetium, rhenium, copper and lutetium or enzymes such as e.g. horseradish peroxidase and alkaline phosphatase are considered as markers according to the invention (see E. Harlow and D. Lane, Antibodies: A Laboratory Manual, Cold Spring Harbor Laboratory Press, Cold Spring Harbor, N.Y. (1988)).

With the detection process according to the invention body fluids or tissue are taken from the animal to be examined, in which the relaxin-like factor is detectable during the animal's pregnancy, before the existence of the factor in the body fluid or in the tissue of the animal is detected by using the antibodies according to the invention in solubilized form or immobilized to a solid carrier. Preferably, the body fluids or tissue are chosen from the group consisting of blood, plasma, serum, urine, milk and follicle fluid.

In particularly preferred versions of the process according to the invention, the above-named specific antibodies are detectable using established assay processes according to classic systems (see e.g. E. Harlow and D. Lane, loc. cit)).

BRIEF DESCRIPTION OF THE DRAWINGS

FIG. 1 shows the primary sequence of the cattle RLF (SEQ ID NO: 1).

FIG. 2 shows a homology comparison between the bovine RLF sequence (SEQ ID NO: 2) and those of the known relaxin molecules of pigs (SEQ ID NO: 9), humans (SEQ ID NO: 10) and mice (SEQ ID NO: 11).

FIGS. 5A–5D show the results of the RT-PCR analyses for RLF- and GAPDH gene transcripts in RNA probes from the noted tissues.

FIGS. 6A–6D show in situ-transcript hybridisation.

Figure 3A:
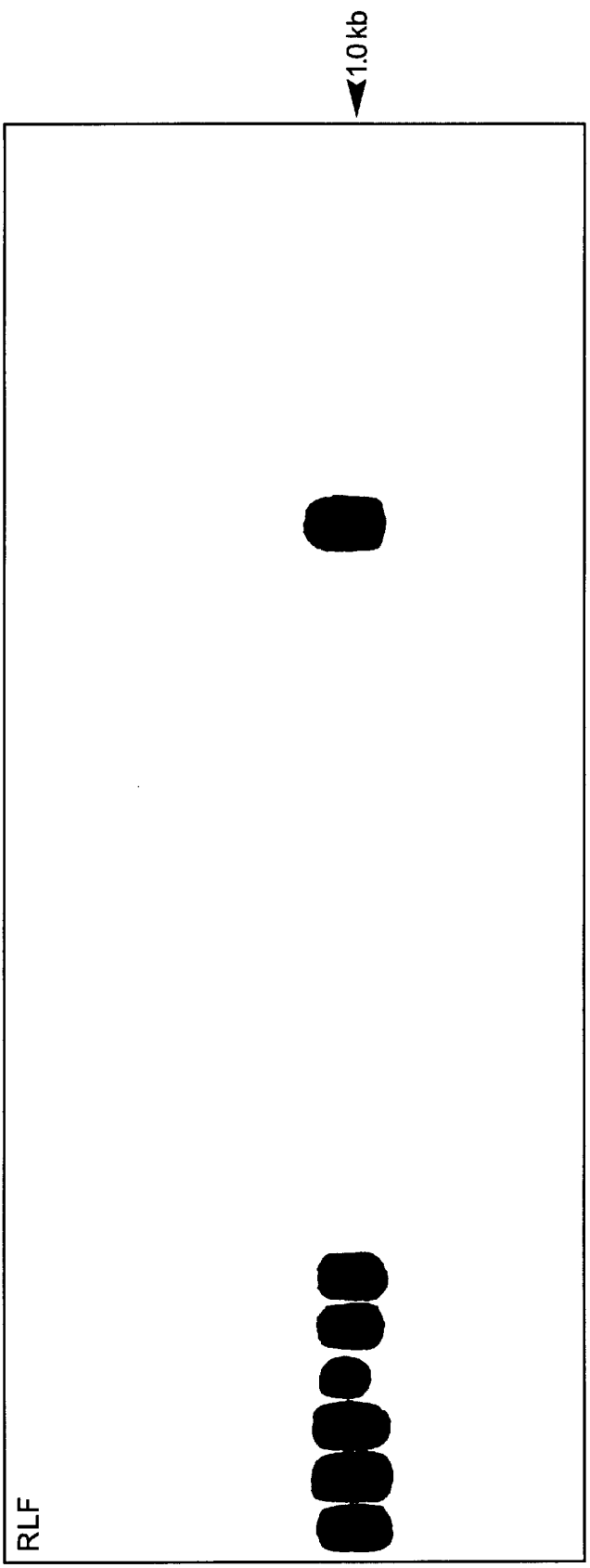
FIGS. 3A and 3B show Northern hybridisations of whole RNA of different bovine tissue.

The invention is explained in detail below with reference to examples.

EXAMPLE 1

Cloning and Sequencing of the Entire Coding Region of the RLF-gene of the Cattle Poly(A)$^+$-enriched RNA was prepared by oligo (dT)—cellulose chromatography of bovine whole RNA of the gonads and used as a template for the preparation of a cDNA library using the ZAP-cDNA-synthesis kit (Stratagene, La Jolla, Calif.). The cDNA was cloned into the vector Uni-ZAP-XR (Stratagene) via the EcoRI and XhoI restriction sites. The complexity of the unamplified library was $1.5 \times 10^6$ pfu and the percentage share of non-recombinants was less than 4%. The average size of the inserts of the cDNA clone was approx. 1.5 kb within a band width of up to >4 kb.

Using the homology region between the published sequences for the RLF-protein of pigs and humans (I. M. Adham et al., Cloning of a cDNA for a novel insulin-like peptide of the testicular Leydig cells, J. Biol. Chem., 268:26668–26672 (1993); E. Burkhardt et al., A human cDNA coding for the Leydig insulin-like peptide (Ley-I-L), Hum. Genet., 94:91–94 (1994)), forward-directed and reverse oligonucleotide primers were prepared (forward directed primer: 5'-CGCTGGTGCGGGTGTGCGG-3'(SEQ ID NO: 3); reverse primers: 5'-GTCTTGCTGGGTGCAGCC-3'(SEQ ID NO: 4)) to obtain a specific probe to screen the cDNA library. These primers were subsequently used in a RT-PCR, 1 μl of the reaction mixture used to prepare the above cDNA library being used as a template for the first-string synthesis. The resulting PCR product of 254 bp was cloned in the vector pGEM T (Promega; Madison, Wis.) and sequenced. This PCR Product was subsequently marked with [α$^{32}$P]dCTP and used to screen approx. 2500 pfu of the bovine testicle cDNA-library using customary hybridisation processes. Three independent cDNA-clones with the longest cDNA-inserts were identified through double-strand DNA-sequencing. As none of the sequences obtained covered the complete 5'-end of the RLF-transcript, a PCR-strategy was used, the T3-polymerase-binding site in the pbluescript-vector of the cDNA-library being used as upstream primer and an internal bovine RLF-specific oligonucleotide (5'-CCGCCAGCCACAGGTCGC-3'(SEQ ID NO: 5)) as downstream primer as well as 5 μl (app. 10000 pfu) of the unamplified cDNA-library as a template. The PCR conditions for 30 cycles in total were as follows: annealing at 65° C., 1 min; elongation at 72° C., 1 min; denaturing at 95° C., 1 min. The products were then conducted to a PCR also comprising 30 cycles, the same downstream primer as well as a new, internal upstream primer (5'-CGAGCGCGCGCACGAAGTGG-3'(SEQ ID NO: 6)) being used. The end-products were electrophoretically separated on a 3% argarose gel and the largest of the DNA fragments obtained were subcloned into the vector PGEM T (Promega) and sequenced. These reactions were repeated for three independent aliquots of the cDNA-library.

To characterize the transcripts which showed positive hybridisation signals vis-à-vis the bovine yellow body, luteal RNA from a late phase of the pregnancy was used to carry out a RT-PCR as was already described above regarding the testicle RNA. The resulting PCR-fragment was cloned and sequenced as described above.

The number of positive clones in the original screening of the bovine testicle cDNA library produced a very high transcript frequency of 0.7%.

The full-length cDNA sequence determined and confirmed using three independent cDNA clones and RT-PCR products is shown in FIG. 1. The transcript of 790 base pairs codes for a polypeptide of 132 amino acids with homologies of 52%, 70% and 87% vis-à-vis the corresponding RLF or LEY-I-L amino acid sequences of mice, humans and pigs. The N-terminus of the protein-coding region has all the features of a signal peptide and is in all probability cleaved off after the alanine radical at position 26. The respective regions for the A-, B- and C-domains as well as for the receptor-binding motif and the 3'-polyadenylisation signal are highlighted.

FIG. 2 shows a homology comparison between the bovine RLF sequence and those of the known relaxin molecules of pigs (SEQ ID NO: 9), humans (SEQ ID NO: 10) and mice (SEQ ID NO: 11). Both the pattern of the preserved cysteine radicals and the putative receptor-binding sequence -R-A-L-V-R- (SEQ ID NO: 12) as well as the high preservation of the A-B-insulin-like peptide domain show similarities. Although the regions which correspond with the known cleavage sites in the relaxin-precursor of the pig also seem to be preserved, there is still however no proof that the RLF molecule is actually cleaved into its A-, B- and C constituents.

EXAMPLE 2

RNA Analysis of Different Tissues

Different tissues of female cattle were chosen such that they covered different stages of the oestrogen cycle and the pregnancy. The preparation of the RNA took place according to conventional processes through extraction with guanidium isothiocyanate and ultra-centrifuging by a CsCl pillow. The preparation of the RNA from the gonad material obtained from the 3-year-old bull took place as described above. After electrophoretic separation of the respective whole RNA and after transfer onto nylon membranes, Northern blots were prepared and hybridized with the radio-actively marked DNA-fragment, comprising specific 254 bp, of the bovine RLF cDNA (see Example 1). For the in-situ hybridisation, additional bovine and ovine testicular tissue was collected from sexually mature animals and prepared for the Bouin-fixing and paraffin embedding described below.

For uterus and other tissue which showed no, or merely weak, signals during the Northern hybridisation, an RT-PCR assay was made using specific, forward-directed and reverse primers (forward-directed primer: 5'-CGCGCTGGTCTTCCGAGG-3'(SEQ ID NO: 7); reverse primer: 5'-GTCTTGCTGGGTGCAGCC-3'(SEQ ID NO: 4)) derived from the bovine cDNA sequence according to FIG. 1, whereby a product of 209 bp was obtained. The primers were made to cover the only splicing site defined for the human gene (E. Burkhardt et al., A human cDNA coding for the Leydig insulin-like peptide (Ley-I-L), Hum. Genet., 94:91–94 (1994) so that a possible contamination of the cDNA-templates by genomic DNA was avoided. The PCR conditions were as described in Example 1. After electrophoretic separation of the PCR products in agarose gels, these were transferred onto nylon membranes (Hybond N; Amersham-Buchler) and hybridised against an internal, radioactive oligonucleotide specific for the bovine RLF-cDNA sequence (5'GGCCCCACAGCCCCTGCCCCAGG-3'(SEQ ID NO: 8)). As a control for the quality of the prepared cDNA, parallel PCR reactions took place using primers which are specific for the bovine GAPDH-mRNA (R. Ivell et al., Oxytocin and oxytocin receptor gene expression in the reproductive tract of the pregnant cow: rescue of luteal oxytocin production at term, Biol. Reprod., 53:553–560 (1995)).

Figure 3B:
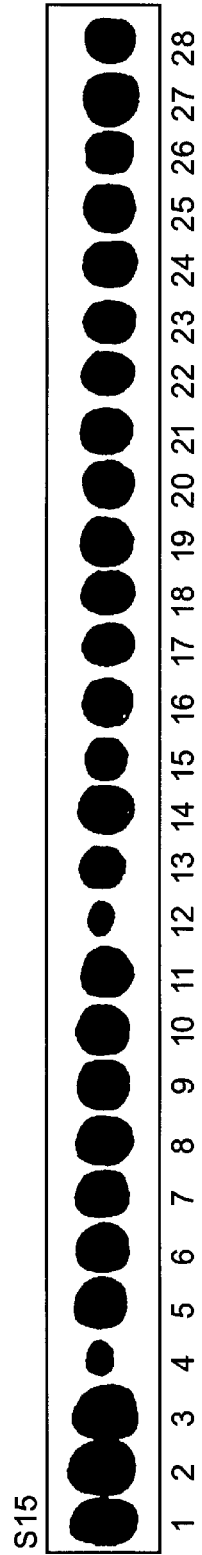
Figures 4A, 4B:
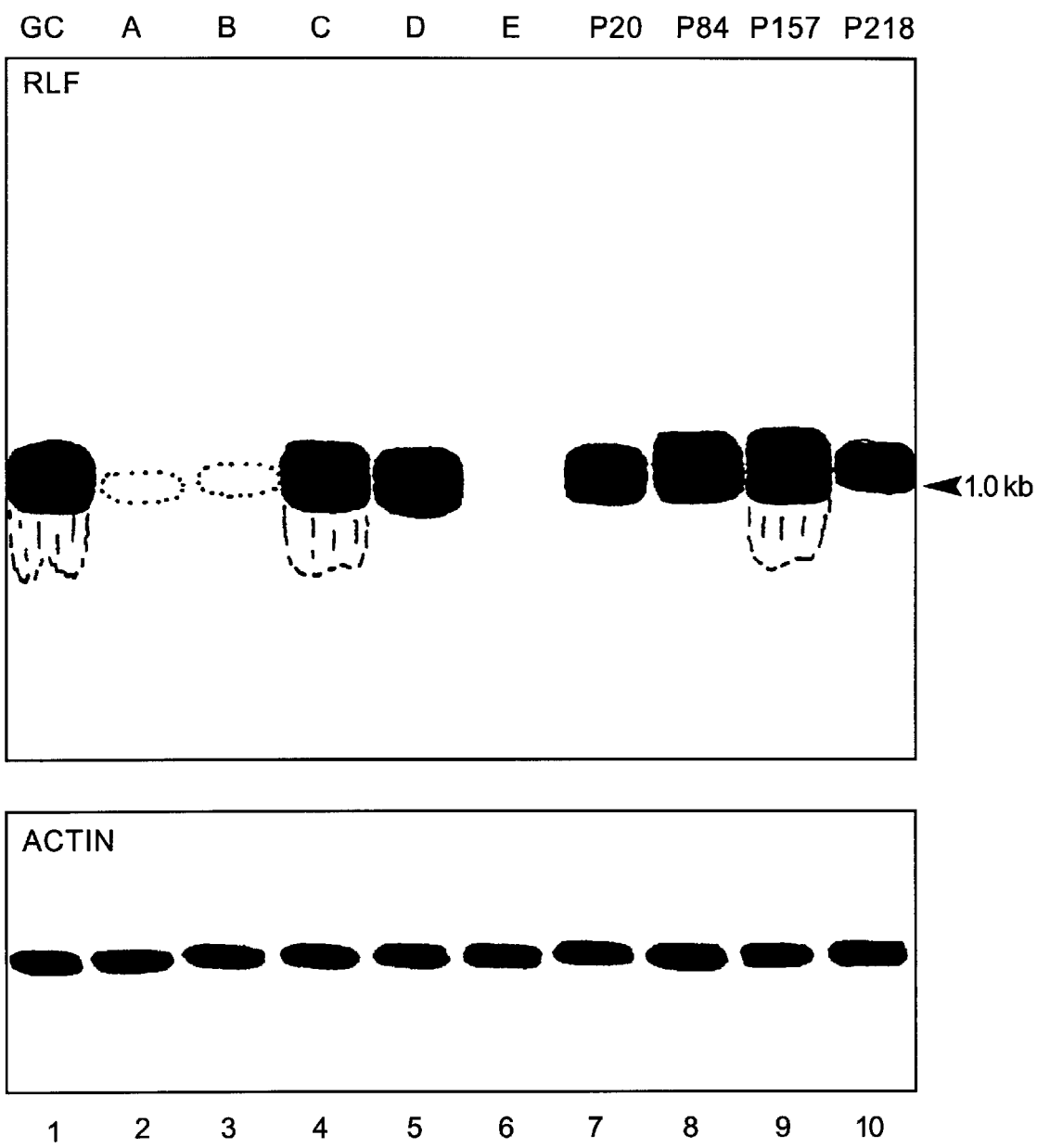
FIGS. 4A and 4B show Northern hybridisations of whole RNA from yellow bodies of different stages of the oestrogen cycle and pregnancy.

A Northern hybridisation of whole RNA of different bovine tissue from both male and female cattle showed as expected a strong signal in the testicles (FIG. 3). Additionally, however, clear signals were also observed in the corpus luteum, the follicular granulous membrane and the theca cells as well as in the ovarian stroma tissue from the oestrogen cycle. Other tissues including that of the endometrium and myometrium both from the stage of the cycle and from the pregnancy and of the fallopian tube, pineal gland, the liver, the heart, the lungs, the spleen, the adrenal gland, the epididymis, the prostate, the thyroid gland, the hypophysis, the cerebellum and cerebral cortex were negative (FIG. 3). The Northern hybridisation of all positive tissues indicated a mRNA of a size of approx. 1.0 kb, which corresponds to a full-length transcript of 790 bases plus roughly 200 bases poly(A)-tail. The results of the Northern hybridisation of whole RNA from different bovine tissues using the fragment comprising 254 bp as a probe are shown in FIG. 3 (picture A). As a control, the blot was rehybridised with a bovine cDNA fragment specific for the ribosomale protein S15 (picture B). The verification of the traces took place with RNA of the following tissue types:

1. ovarian stroma
2. theca cells
3. granulous membrane cells
4. corpus luteum of the middle phase of pregnancy (day 150)
5. corpus luteum of the late cycle phase (approx. day 17)
6. corpus luteum of the middle cycle phase (day 7)
7. myometrium of the late phase of pregnancy (day 280)
8. myometrium of the middle phase of pregnancy (day 150)
9. myometrium of the middle cycle phase (day 7)
10. myometrium of the oestrus (day 0)
11. endometrium of the late phase of pregnancy (day 280)
12. endometrium of the middle phase of pregnancy (day 150)
13. endometrium of the middle cycle phase (day 7)
14. endometrium of the oestrus (day 0)
15. cerebral cortex
16. cerebellum
17. hypophysis
18. thyroid gland
19. prostate
20. epididymis
21. testicles
22. suprarenal gland
23. spleen
24. lung
25. heart
26. liver
27. fallopian tube
28. pineal gland The Northern hybridisation of whole RNA from yellow bodies of different stages of the oestrogen cycle and pregnancy (FIG. 4) confirms the relatively high expression in granulous membrane cells freshly prepared from pre-ovulatory follicles. Inside the yellow body, there is a clear increase in the specific RLF-mRNA in the second half of the oestrogen cycle, maximum values being reached in the middle phase of pregnancy. In the late phase of pregnancy the RLF-mRNA seems to be reduced. In the corpus albicans, the RLF-mRNA is not detectable even after extended exposure time. Results from the Northern hybridisation using a specific bovine RLF-cDNA probe of whole RNA from granulous membrane cells (GC) and yellow bodies from different stages of the cycles and pregnancy are shown in FIG. 4A. To monitor the uniform loading with RNA, the blot was rehybridised with an actin probe (picture B). The code letters used in FIG. 4 have the following meaning:

A=days 2–3 of the early cycle phase
B=days 4–6 of the early middle cycle phase
C=days 8–14 of the middle cycle phase
D=days 15–18 of the late cycle phase
E=corpus albicans
P=pregnancy, the figures giving the days of pregnancy An RT-PCR analysis was used to examine other bovine tissues such as in particular those which are associated with relaxin-determined physiology during pregnancy. The results of the RT-PCR analyses for RLF- and GAPDH gene transcripts in RNA probes from the stated tissues are given in FIG. 5. The code numbers of the traces have the following meanings:

C=control
1=corpus luteum of the late phase of pregnancy (day 280)
2=myometrium of the late phase of pregnancy (day 280)
3=myometrium of the middle phase of pregnancy (day 150)
4=myometrium of the middle cycle phase (day 7)
5=myometrium of the oestrus (day 0)
6=endometrium of the late phase of pregnancy (day 280)
7=endometrium of the middle phase of pregnancy (day 150)
8=endometrium of the middle cycle phase (day 7)
9=endometrium of the oestrus (day 0)
10=epididymis
11=testicles
12=hypothalamus
13=heart
14=lung
15=caruncle of the late phase of pregnancy (day 280)
16=placenta flaps of the late phase of pregnancy (day 280)
17=amnion of the late phase of pregnancy (day 280)
18=chorion of the late phase of pregnancy (day 280)

The controls show parallel reactions, in which RNA was replaced by water.

Figures 5A, 5B:
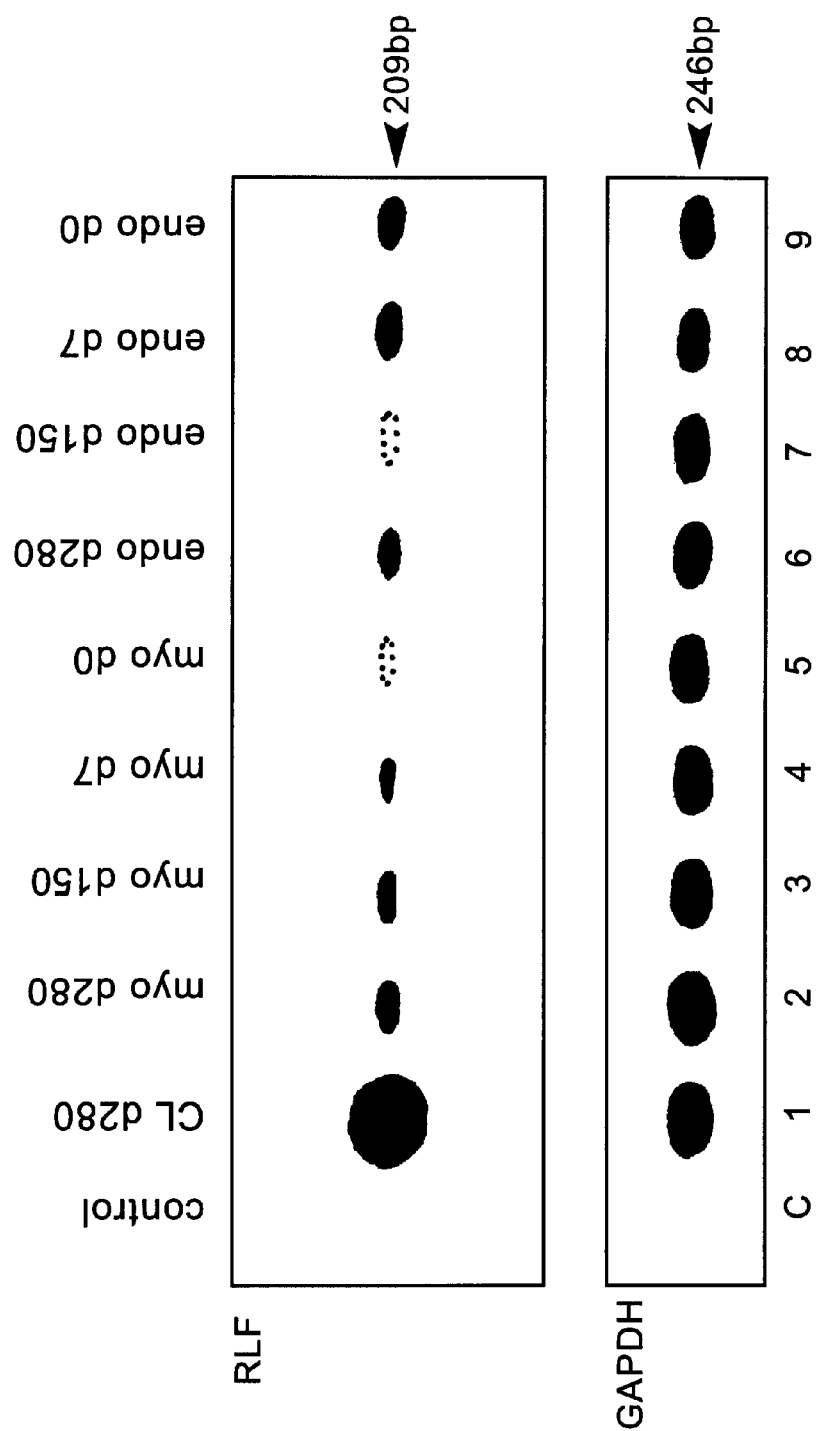

Although the technique which forms the basis of FIG. 5 is merely semi-quantitative, there are very weak positive signals in most tissues. As expected, the probes from bovine corpus luteum and testicles used as positive controls produced very strong signals. Interestingly a signal of medium strength was also observed in the bovine hypothalamus.

In Situ-transcript Hybridisation

Testicle and ovarian fragments were fixed for 6 hours in Bouin's solution, washed in 70% ethanol and embedded in paraffin wax. Sections with a thickness of 10 μm were then conducted to a non-radioactive hybridisation essentially according to Maguire et al. (S. M. Maguire et al., Stage-dependent expression of mRNA for cyclic protein 2 during spermatogenesis is modulated by elongate spermatids, Mol. Cell. Endocrinol., 94:79–88 (1993)), cRNA probes marked by in-vitro transcription of the original product cloned by means of PCR (s.a.) being used in the presence of digoxigenin-UTP (Boehringer-Mannheim, Mannheim, FRG). The negative controls took place in parallel using the sense-strand cRNA. The sections were lightly counter-coloured with methyl green.

Figure 6A:
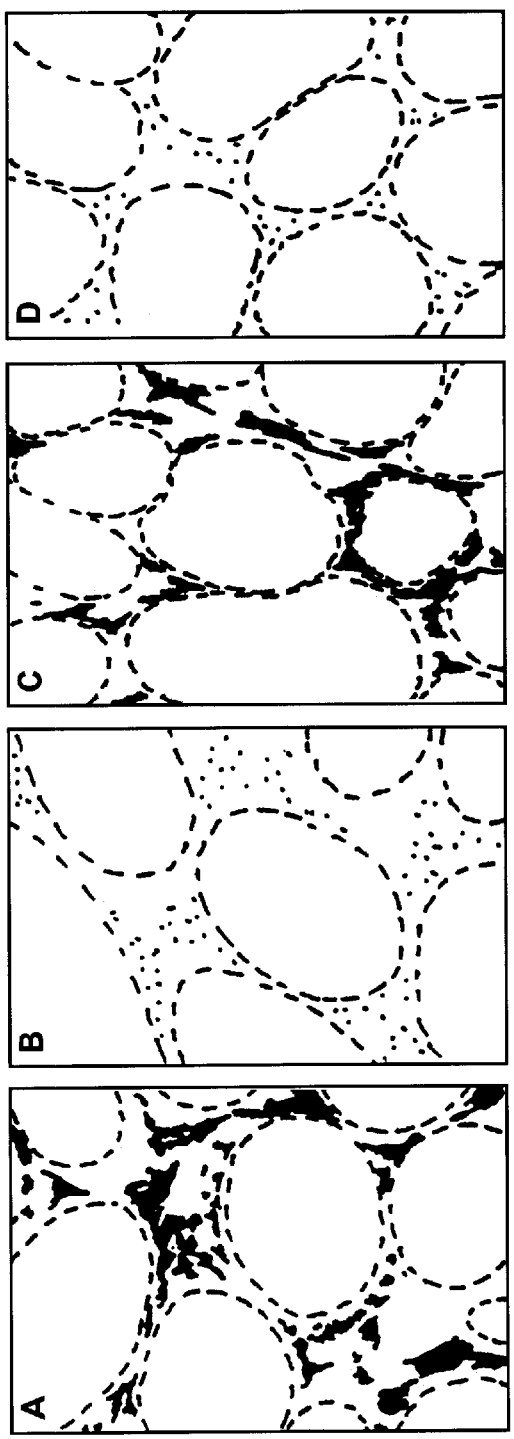
Figure 6B:
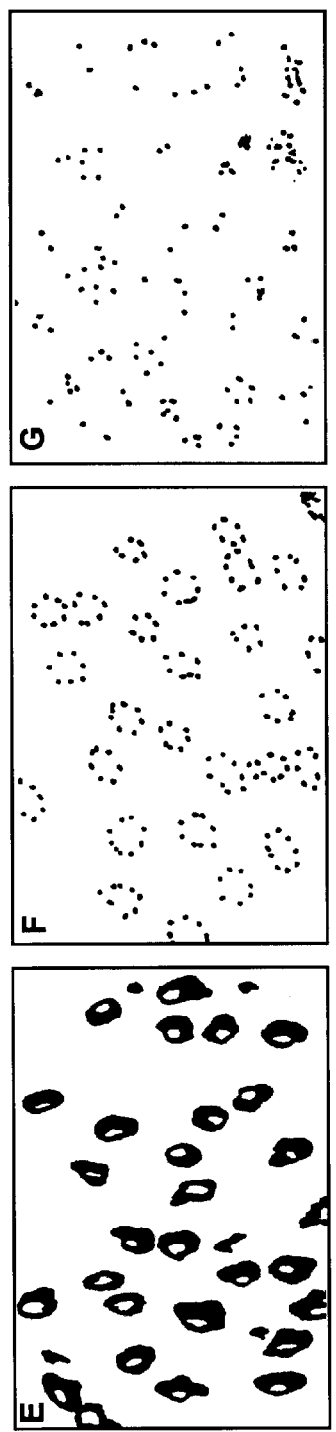

The corresponding results are shown in FIG. 6.

The letters used in FIG. 6 have the following meaning:
A—adult bovine testicle (anti-sense probe, X 200).
B—adult bovine testicle (sense probe as control, X 200).
C—adult ovine testicle (anti-sense probe, X 200).
D—adult ovine testicle (sense probe as control, X 200).
E—corpus luteum (middle—late cycle phase; anti-sense probe, X 400).
F—corpus luteum (middle—late cycle phase; sense probe as control, X 400).
G—corpus luteum (late cycle phase; anti-sense probe, X 200).
H—healthy antral-follicle (early cycle phase; anti-sense probe, X 200; GC granulous membrane cell layer; TI, theca interna
I—as in H, but using a sense probe as control.
J—healthy pre-ovulatory follicle (late cycle phase; anti-sense probe, X 200).
K—atretic follicle (middle cycle phase; sense probe as control; X 200).
L—As in K, but using an anti-sense probe.
M—As in K, but histologically, coloured with haemotoxilin-eosin only.

The sections of the corpus luteum shown in E-G required a much more stringent washing to remove unspecific background, which led to weaker specific signals with the anti-sense probe vis-à-vis the other sections.

The results show that in both bovine as well as oyine testicles (FIGS. 6A and C) the RLF gene transcripts are detected in the Leydig cells exclusively, as has also been shown in other species. Inside the ovary (FIGS. 6E–M), a strongly positive signal appears in the theca cell layer of large antral follicles from the early and late cycle phases (FIGS. 6H and J) as well as in the corpus luteum of the middle to late cycle phase (FIG. 6E). Both stroma cells and follicular granulous membrane cells seem to be negative when using this technique and accordingly do not stand out from the negative control sections using the sense-cRNA probe (FIGS. 6F, I and K).

What is claimed is:

1. A diagnosis aid for detecting pregnancy in cattle, comprising an isolated and purified polyclonal antibody raised to SEQ ID NO:2.

2. A process for detecting pregnancy in cattle, comprising removing a body fluid or tissue sample from said cattle to be examined, contacting a diagnosis aid of claim 1 with said fluid or sample under conditions where said diagnosis aid will bind to at least one of a relaxin-like factor in said fluid or sample, a fragment of said factor and an active derivative of said factor, when present, to form a complex, and detecting the presence of said complex with a detection agent, wherein the presence of said complex is indicative of the pregnancy of said cattle.

3. A process according to claim 2 wherein said body fluid or tissue sample is selected from the group consisting of blood, plasma, serum, urine, milk and follicle fluid.

4. A process according to claim 2, wherein the presence of said complex is detected by radioimmunoassay.

5. A process according to claim 2, wherein the presence of said complex is detected by enzyme-coupled immunoassay.

6. A process for detecting pregnancy in cattle, comprising removing a body fluid or tissue sample from said cattle to be examined, contacting a diagnosis aid of claim 1 with said fluid or sample under conditions where said diagnosis aid will bind to a relaxin-like factor in said fluid or sample, when present, to form a complex, and detecting the presence of said complex with a detection agent, wherein the presence of said complex is indicative of the pregnancy of said cattle.

7. A process according to claim 6 wherein said body fluid or tissue sample is selected from the group consisting of blood, plasma, serum, urine, milk and follicle fluid.

8. A process according to claim 6, wherein the presence of said complex is detected by radioimmunoassay.

9. A process according to claim wherein the presence of said complex is detected by enzyme-coupled immunoassay.

10. An isolated and purified polyclonal antibody raised to SEQ ID NO:2.

11. An antibody according to claim 10, further comprising a detectable marker.

12. A process of detecting pregnancy in cattle comprising removing a body fluid or tissue sample from said cattle to be examined contacting an antibody of claim 10 with said fluid or sample under conditions where said antibody will bind to a relaxin-like factor or a fragment of said factor or an active derivative of said factor, when present, to form a complex, and detecting the presence of said complex with a detection agent, wherein the presence of said complex is indicative of the pregnancy of said cattle, wherein said fragment of the relaxin-like factor and said active derivative of the relaxin-like factor have the same immunogenicity as the relaxin-like factor.

13. A process for detecting pregnancy in cattle, comprising removing a body fluid or tissue sample from said cattle to be examined, contacting an antibody of claim 10 with said fluid or sample under conditions where said antibody will bind to a relaxin-like factor in said fluid or sample, when present, to form a complex, and detecting the presence of said complex with a detection agent, wherein the presence of said complex is indicative of the pregnancy of said cattle.

* * * * *